United States Patent
Lawson et al.

(10) Patent No.: US 11,633,344 B2
(45) Date of Patent: Apr. 25, 2023

(54) OXIDATIVE HAIR CREAM COMPOSITION CONTAINING THIOPHENE AZO COLORANT

(71) Applicant: Milliken & Company, Spartanburg, SC (US)

(72) Inventors: Richard Lawson, Greer, SC (US); Haihu Qin, Greer, SC (US); Steven Spanhove, Boortmeerbeek (BE); Laurent De Bruyne, Gentbrugge (BE); Sanjeev Dey, Spartanburg, SC (US)

(73) Assignee: Miliken & Company, Spartanburg, SC (US)

(*) Notice: Subject to any disclaimer, the term of this patent is extended or adjusted under 35 U.S.C. 154(b) by 0 days.

(21) Appl. No.: 17/723,591

(22) Filed: Apr. 19, 2022

(65) Prior Publication Data

US 2022/0241178 A1 Aug. 4, 2022

Related U.S. Application Data

(63) Continuation of application No. 17/470,817, filed on Sep. 9, 2021, now Pat. No. 11,351,106.

(60) Provisional application No. 63/077,740, filed on Sep. 14, 2020.

(51) Int. Cl.
*A61Q 5/10* (2006.01)
*A61K 8/84* (2006.01)
*A61K 8/22* (2006.01)

(52) U.S. Cl.
CPC ............... *A61K 8/84* (2013.01); *A61K 8/22* (2013.01); *A61Q 5/10* (2013.01); *A61K 2800/4322* (2013.01)

(58) Field of Classification Search
CPC . A61Q 5/10; A61Q 5/065; A61K 8/22; A61K 2800/4322; A61K 8/4986; A61K 8/4913
USPC .......................................................... 8/437
See application file for complete search history.

(56) References Cited

U.S. PATENT DOCUMENTS

| | | | |
|---|---|---|---|
| 5,688,291 A | 11/1997 | Said | |
| 5,789,560 A | 8/1998 | Etzbach | |
| 6,306,182 B1 | 10/2001 | Chan | |
| 7,056,355 B2 * | 6/2006 | Pratt | A61Q 5/10 8/405 |
| 7,083,655 B2 * | 8/2006 | Pratt | A61K 8/466 8/405 |
| 7,189,265 B2 | 3/2007 | Said | |
| 8,785,361 B2 | 7/2014 | Sivik | |
| 9,068,081 B2 | 6/2015 | Torres | |
| 9,163,146 B2 | 10/2015 | Torres | |
| 9,820,922 B1 | 11/2017 | Singer | |
| 2002/0050012 A1 | 5/2002 | Orr | |
| 2003/0110977 A1 | 6/2003 | Batlaw | |
| 2004/0143910 A1 * | 7/2004 | Said | A61K 8/368 8/405 |
| 2005/0235433 A1 | 10/2005 | Rondeau | |
| 2011/0154583 A1 | 6/2011 | Lewis | |

FOREIGN PATENT DOCUMENTS

| | | |
|---|---|---|
| EP | 1366752 A1 | 12/2003 |
| EP | 3015134 | 5/2016 |
| EP | 304701 | 7/2016 |
| EP | 3021830 B1 | 4/2018 |
| EP | 3397236 A1 | 11/2018 |
| EP | 3397345 A1 | 11/2018 |
| EP | 3397346 A1 | 11/2018 |
| EP | 3019150 B1 | 4/2020 |
| FR | 2456764 A2 | 12/1980 |
| GB | 2217735 | 11/1989 |
| WO | 2006134051 A1 | 12/2006 |
| WO | 2009090122 A2 | 7/2009 |
| WO | 2012022709 A1 | 2/2012 |
| WO | 2015031418 A1 | 3/2015 |
| WO | 2015042209 A1 | 3/2015 |
| WO | 2017055254 A1 | 4/2017 |
| WO | 2017117522 A1 | 7/2017 |
| WO | 2017117543 A1 | 7/2017 |
| WO | 2017117552 A1 | 7/2017 |
| WO | 2017172516 A1 | 10/2017 |
| WO | 2017197099 A1 | 11/2017 |

OTHER PUBLICATIONS

Dawson et al: "Poly(vinylamine hydrochloride). Synthesis and utilization for the preparation of water-soluble polymeric dyes", Journal of the American Chemical Society, American Chemical Society, vol. 98, No. 19, Sep. 15, 1976 (Sep. 15, 1976), pp. 5996-6000, XP002558622, ISSN: 0002-7863, DOI: 10.1021/JA00435A036.

Guthrie, J T: "Polymeric Colorants", Review of Progress in Coloration, Society of Dyers and Colourists. Bradford, GB, vol. 20, Jan. 1, 1990 (Jan. 1, 1990), pp. 40-52, XP000651083, ISSN: 0557-9325.

International Search Report and Written Opinion for App. No. PCT/US2021/049774, dated Feb. 2, 2022, 15 pages.

International Search Report and Written Opinion for App. No. PCT/US2021/049775, dated Feb. 7, 2022, 15 pages.

International Search Report and Written Opinion for App. No. PCT/US2021/049776, dated Feb. 10, 2022, 17 pages.

Shen et al: "Synthesis, Characterisation and properties of Ethoxylated Azo Dyes", Feb. 21, 2003 (Feb. 21, 2003), XP055880592, 6 pages, Retrieved from the Internet: URL:https://www.koreascience.or.kr/article/JAK0200311921587175.pdf [retrieved on Jan. 18, 2022].

STIC Search Report dated Feb. 4, 2022, 688 pages.

(Continued)

*Primary Examiner* — Eisa B Elhilo

(74) *Attorney, Agent, or Firm* — Brenda D. Wentz

(57) ABSTRACT

This invention relates to an oxidative hair cream composition that contains at least one oxidative hair cream ingredient and at least one thiophene azo colorant.

15 Claims, No Drawings

(56) References Cited

OTHER PUBLICATIONS

Wang Dongrui et al, "Amphiphilic azo polymers: Molecular engineering, self-assembly and photoresponsive properties", Progress in Polymer Science, Pergamon Press, Oxford, GB, (Jul. 16, 2012), vol. 38, No. 2, doi:10.1016/J.PROGPOLYMSCI.2012.07.003, ISSN 0079-6700, pp. 271-301, XP028980021.

* cited by examiner

OXIDATIVE HAIR CREAM COMPOSITION CONTAINING THIOPHENE AZO COLORANT

CROSS REFERENCE TO RELATED APPLICATIONS

This application is a continuation of and claims priority to U.S. patent application Ser. No. 17/470,817, entitled "Oxidative Hair Cream Composition Containing Thiophene Azo Colorant," which was filed on Sep. 9, 2021, which claims priority to U.S. Provisional Patent Application No. 63/077,740, entitled "Oxidative Hair Cream Composition Containing Thiophene Azo Colorant," which was filed on Sep. 14, 2020, both of which are entirely incorporated by reference herein.

TECHNICAL FIELD

This invention relates to an oxidative hair cream composition that contains at least one oxidative hair cream ingredient and at least one thiophene azo colorant.

BACKGROUND

Human hair is arbitrarily assigned a scale with different levels that describe its darkness (or lightness). Black hair is designated as level one, medium brown hair as level five, and pale light blond as level ten, with several nuances in between. Hair bleaching is a chemical process by which the melanin pigment granules are gradually destroyed by the bleaching agent, resulting in lighter hair color. The melanin pigments are not all lightened at the same rate. The eumelanins are easier to break down than the pheomelanins. Because of this property, dark hair, when bleached, experiences preferential destruction of the melanin pigments, which leads to the visual enhancement of the red pigments and the casting of an undesirable warm reddish orange or "brassy" tone to the bleached hair. In order to neutralize the warmth, hair colorants of a drabbing nature are almost always applied during or after a bleaching treatment.

Based on their chemical composition and their strength, hair bleaches may be classified into two groups, designated as Category 1 and Category 2. Category 1 bleaches are liquid- or cream-based compositions utilizing alkaline hydrogen peroxide solutions as the main oxygen-generating agent to oxidize and bleach hair melanin, usually in conjunction with a hair coloring process. Just before use, the peroxide is mixed with an alkalizing agent such as ammonia, and the resulting liquid or cream is applied to hair for 30 to 60 minutes. Such compositions may lighten the hair by as much as four levels, depending on the concentration of hydrogen peroxide used. For example, a level-6 hair may be lightened to a level 10, under favorable conditions.

Category 2 bleaches are generally powder compositions, some in cream form, which are based on persulfate salts—(ammonium, potassium, sodium) as auxiliary or booster supplies of active oxygen—and silicate and/or carbonate salts which serve as sources of alkalinity. Similar to Category 1 bleaches, they are mixed just prior to use with hydrogen peroxide solutions to form a workable cream that can be applied to the hair. It is possible to incorporate hydrogen peroxide itself into the powder bleach in a solid form, and all that is needed to achieve a workable cream is to add water to the powder. Quite often, a third separately packaged component, referred to as a bleach oil, is added to the bleach powder and peroxide at time of use. Bleach oil may contain humectants and other conditioning agents. Category 2 bleaches can deliver over seven levels of lift, something which cannot be attained with Category 1 bleaches. They are usually utilized whenever more than four levels of lift are desired, such as when lifting a level-5 hair, or darker, to a pale blond.

Because of the underlying warm tones that are exposed at various levels of bleaching, a toning process to neutralize the warmth and give the hair a pleasant natural look generally accompanies hair lightening. Toners fall into three hues: blue-green, blue, and violet, generally known as drabbing or ashing hues. These hues, or combinations thereof, are recommended to neutralize the spectrum of undertones that are exposed during the lightening process. Light brown hair, for example, would expose yellow undertones upon bleaching. Therefore, according to the law of color, a violet-based toner would neutralize the yellowish hue to result in a platinum or silver blond shade. The concentration of the toner should be adjusted so that the lift is not masked by the deposition of color.

In accordance with present invention, there is a single-step process using a composition of hair bleach that can simultaneously lighten the hair and effectively deposit various shades of color. This is achieved by including dyes in the bleach composition. A suitable dye for this application needs to be: (a) have a desirable blue-violet hue to neutralize the yellowish hue, (b) stable in the bleach, (c) has a good toxicity profile and (d) easily mixed into and remain homogeneous in the oxidative composition.

Thus, there is a continuous need for improved colorants for this application. The thiophene azo dyes disclosed herein and the oxidative hair care compositions comprising same offer advantages over previous efforts in this area, such as better lifting, better hue, better mixing with hair cream composition, and improved toxicity profiles.

BRIEF SUMMARY

In one aspect, the invention relates to an oxidative hair cream composition, wherein the composition comprises at least one thiophene azo colorant and at least one oxidative hair cream ingredient.

In a further aspect of the invention, the thiophene azo colorant is a dye according to Formula I:

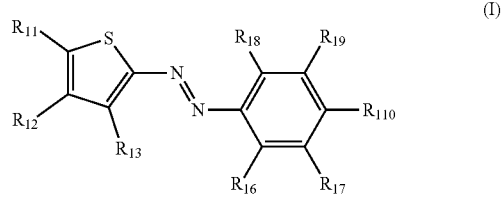

(I)

wherein each $R_{11}$ to $R_{110}$ group is independently selected from the group consisting of hydrogen, deuterium and $R^v$; each $R^v$ is independently selected from the group consisting of halogens, nitro, nitrile, alkyl, substituted alkyl, alkenyl, substituted alkenyl, aryl, substituted aryl, alkynyl, substituted alkynyl, —$(CH_2)_n$—O—$R^x$, —$(CH_2)_n$—$NR^xR^y$, —$C(O)R^x$, —$C(O)OR^x$, —$C(O)O^-$, —$C(O)NR^xR^y$, —OC(O)$R^x$, —OC(O)$OR^x$, —OC(O)$NR^xR^y$, —$S(O)_2R^x$, —$S(O)_2OR^x$, —$S(O)_2O^-$, —$S(O)_2NR^xR^y$, —$NR^xC(O)R^y$, —$NR^xC(O)OR^y$, —$NR^xC(O)SR^y$, —$NR^xC(O)NR^yR^z$, —$OR^x$, —$NR^xR^y$, —$P(O)_2R^x$, —$P(O)(OR^x)_2$, —$P(O)(OR^x)O^-$, and —$P(O)(O^-)_2$; wherein the index n is an integer from 0 to 4; and wherein $R^x$, $R^y$ and $R^z$ are independently selected from the group consisting of hydrogen, alkyl, substituted alkyl, alkenyl, substituted alkenyl, aryl, substituted aryl, alkynyl, substituted alkynyl, and $R^u$; $R^u$ is an organic group composed of one or more organic monomers with said monomer molecular weights ranging from 28 to 500.

In yet a further aspect of the invention, the at least one thiophene azo colorant is a dye according to the following structure:

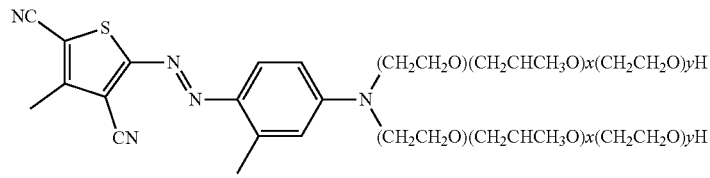

wherein each x and y are independently integers from 0 to 20.

In another aspect, the invention relates to a method for treating hair comprising the steps of: (a) providing an oxidative hair cream composition, wherein the composition comprises at least one thiophene azo colorant and at least one oxidative hair cream ingredient, and (b) contacting the oxidative hair cream composition with human hair.

DETAILED DESCRIPTION

The invention described herein is an oxidative hair cream that contains at least one oxidative hair cream ingredient and at least one coloring agent that contains a thiophene azo chromophore. The thiophene azo colorant-containing oxidative hair cream is suitable for direct application to hair (such as human hair, animal hair, and the like) and provides improvements in stability and shading over prior art hair dyes.

As used herein, the term "hair" is intended to include keratin fiber such as human hair, animal hair, and the like.

As used herein, the term "alkoxy" is intended to include $C_1$-$C_8$ alkoxy and alkoxy derivatives of polyols having repeating units such as butylene oxide, glycidol oxide, ethylene oxide or propylene oxide.

As used herein, the terms "polyalkyleneoxy" and "polyoxyalkylene," as used interchangeably herein, generally refer to molecular structures containing the following repeating units: —$CH_2CH_2O$—, —$CH_2CH_2CH_2O$—, —$CH_2CH_2CH_2CH_2O$—, —$CH_2CH(CH_3)O$—, —$CH_2CH_2CH(CH_3)O$—, and any combinations thereof. Furthermore, the polyoxyalkylene constituent may be selected from the group consisting of one or more monomers selected from a $C_{2-20}$ alkyleneoxy group, a glycidol group, a glycidyl group, or mixtures thereof.

As used herein, unless otherwise specified, the terms "alkyl" and "alkyl capped" are intended to include $C_2$ to $C_{100}$ alkyl groups, $C_2$ to $C_{50}$ alkyl groups, $C_5$-$C_{25}$ alkyl groups, or even $C_{10}$-$C_{20}$ alkyl groups.

As used herein, unless otherwise specified, the term "aryl" is intended to include $C_5$-$C_{18}$ aryl groups and, in one aspect, $C_5$-$C_{12}$ alkyl groups.

As used herein, unless otherwise specified, the term "alkyl" is intended to include $C_1$-$C_{18}$ alkyl groups and, in one aspect, $C_1$-$C_6$ alkyl groups.

As used herein, unless otherwise specified, the term "alkanoyl" refers to univalent groups of the formula —C(O)$R^a$, where $R^a$ is an alkyl group, preferably a $C_3$-$C_{29}$ alkyl group.

As used herein, unless otherwise specified, the term "alkenyl" refers to univalent groups derived from acyclic olefinic hydrocarbons by removal of a hydrogen atom from any carbon atom. In the context of this definition, the term "acyclic olefinic hydrocarbons" refers to acyclic hydrocarbons containing one or more carbon-carbon double bonds.

A used herein, unless otherwise specified, the term "alkenoyl" refers to univalent groups of the formula —C(O)$R^b$, where $R^b$ is an alkenyl group, preferably a $C_3$-$C_{29}$ alkenyl group.

A used herein, unless otherwise specified, the term "aroyl" refers to univalent groups of the formula —C(O)$R^c$, where $R^c$ is an aryl group, preferably a $C_6$-$C_{10}$ aryl group.

The terms "ethylene oxide," "propylene oxide" and "butylene oxide" may be shown herein by their typical designation of "EO," "PO" and "BO," respectively.

All percentages and ratios are calculated by weight unless otherwise indicated. All percentages and ratios are calculated based on the total composition unless otherwise indicated.

In the present invention, the oxidative hair cream composition includes at least one oxidative hair cream ingredient. Oxidative hair cream ingredients include, for example but not limited to, oxidizing agents, emollient oils, surfactants which may include nonionic, anionic, cationic, zwitterionic, betaine surfactants, polar solvents, chelating agents, pH adjusters, conditioning agents, and other ingredients and mixtures thereof. Oxidizing agents may be selected from the group consisting of hydrogen peroxide. Hydrogen peroxide may be present in an amount in the range from 0.01% to 33% by weight of the total composition, or even 0.1% to 15% by weight of the total composition.

The hair cream composition of the invention is generally aqueous based comprising from about 0.01-99%, preferably from about 0.1-98%, more preferably from about 45 to 95% by weight of the total composition of water.

Emollient Oils

If desired the hair cream composition may contain one or more emollient oils. Such oils will provide a conditioning effect to the hair. If present, such oils may range from about 0.001 to 45% preferably from about 0.01 to 40%, more preferably from about 0.1 to 35% by weight of the total composition. Suitable oils include silicones such as dimethicone, phenyl silicones, fatty alkyl silicones such as cetyl or stearyl dimethicone, or silicone surfactants which are generally referred to as dimethicone copolyols, or cetyl dimethicone copolyol. Also suitable are various animal, vegetable, or mineral oils derived from plants or animals, or synthetic oils. Examples include oils from sunflower, castor seeds, orange, lemon, jojoba, mineral oil, and the like. Common other examples would include cetearyl alcohol, lauryl alcohol, myristyl alcohol, lanolin alcohol, coconut alcohol, and the like.

Surfactants

The oxidative dye composition may comprise one or more surfactants. Suitable surfactants include anionic surfactants, nonionic surfactants, amphoteric surfactants, and the like. If present, surfactants may range from about 0.001-50%, preferably about 0.005-45%, more preferably about 0.1-40% by weight of the first composition.

Nonionic Surfactants

Examples of nonionic surfactants include alkoxylated alcohols or ethers, alkoxylated carboxylic acids, sorbitan derivatives, and the like. Alkoxylated alcohols, or ethers, are formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include steareth 2-30, which is formed by the reaction of stearyl alcohol and ethylene oxide where the number of repeating ethylene oxide units is 2 to 30; laureth 2-30, which is formed by the reaction of lauryl alcohol and ethylene oxide where the number of repeating ethylene oxide units is 2 to 30; Oleth 2-30 which is formed by the reaction of oleyl alcohol and ethylene oxide where the number of repeating ethylene oxide units is 2 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. Particularly preferred is where the nonionic surfactant is steareth-20 or cetearth-20. Also suitable are alkyoxylated carboxylic acids, which are formed by the reaction of a carboxylic acid with an alkylene oxide or with a polymeric ether.

Also suitable are various types of alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20-85, sorbitan oleate, sorbitan palmitate, sorbitan sesquiisostearate, sorbitan stearate, and so on. In one preferred embodiment Polysorbate 20 is preferred.

Anionic Surfactants

The hair cream composition may optionally contain one or more anionic surfactants. Preferred ranges of anionic surfactant are about 0.01-25%, preferably 0.5-20%, more preferably 1-15% by weight of the total oxidative composition. Suitable anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula: $R_1-SO_3-M$ wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide, or fatty acids reacts with alkanolamines or ammonium hydroxides. The fatty acids may be derived from coconut oil, for example. Examples of fatty acids also include lauric acid, stearic acid, oleic acid, palmitic acid, and so on.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones, which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula: wherein $R_1$ is a $C_{8-24}$ alkyl or alkenyl radical, preferably $C_{10-18}$; $R_2$ is H, $C_{1-4}$ alkyl, phenyl, or $-CH_2COOM$; $R_3$ is $CX_2-$ or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Cationic, Zwitterionic or Betaine Surfactants

Certain types of amphoteric, zwitterionic, or cationic surfactants may also be used as the amphiphilic surface active material. Descriptions of such surfactants are set forth in U.S. Pat. No. 5,843,193, which is hereby incorporated by reference in its entirety.

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula $R-NH(CH_2)_nCOOM$ or iminodialkanoates of the formula: $R-[(CH_2)_mCOOM]_2$ and mixtures thereof, wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates. Zwitterionic surfactants are also suitable for use in the compositions of the invention and include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, and the like. Particularly preferred is cocamidopropyl-betaine.

Polar Solvents

The hair cream composition may also comprise a variety of nonaqueous polar solvents other than water, including mono-, di-, or polyhydric alcohols, and similar water soluble ingredients. If present, such polar solvents may range from about 0.01-25%, preferably about 0.05-15%, more preferably about 0.1-10% by weight of the first composition of polar solvent. Examples of suitable monohydric alcohols include ethanol, isopropanol, benzyl alcohol, butanol, pentanol, ethoxyethanol, and the like. Examples of dihydric, or polyhydric alcohols, as well as sugars and other types of humectants that may be used include glycerin, glucose, fructose, mannose, mannitol, malitol, lactitol, inositol, and the like. Suitable glycols include propylene glycol, butylene glycol, ethylene glycol, polyethylene glycols having from 4 to 250 repeating ethylene glycol units, ethoxydiglycol, and the like.

Chelating Agents

The oxidative dye composition may optionally contain 0.0001-5%, preferably 0.0005-3%, more preferably 0.001-2% of one or more chelating agents which are capable of complexing with and inactivating metallic ions in order to prevent their adverse effects on the stability or effects of the composition. In particular, the chelating agent will chelate the metal ions found in the water and prevent these ions from interfering with the deposition and reaction of the dye with the hair fiber surface. Suitable chelating agents include EDTA and calcium, sodium, or potassium derivatives thereof, HEDTA, sodium citrate, TEA-EDTA, and so on.

pH Adjusters

It may also be desirable to add small amounts of acids or bases to adjust the pH of the oxidative dye composition to the desired pH range. Suitable acids include hydrochloric acid, phosphoric acid, etidronic acid, and the like. Suitable bases include sodium hydroxide, ammonium hydroxide, potassium hydroxide, and the like. Also suitable are primary, secondary, or tertiary amines or derivative thereof such as aminomethyl propanol, monoethanolamine, and the like. Phosphate salts such as potassium phosphate, disodium phosphate, and the like may also be used. Suggested ranges of pH adjusters are from about 0.00001-8%, preferably about 0.00005-6%, more preferably about 0.0001-5% by weight of the total composition.

Conditioning Agents

Hair cream compositions may also include a hair conditioning agent. Suitable conditioning agents for use herein include, but are not limited to, cationic surfactants, insoluble silicones, non-volatile hydrocarbons, non-volatile hydrocarbon esters, and mixtures thereof.

Preferred conditioning agents for use herein include cationic surfactants, cationic polymers, insoluble silicone conditioning agents, amino functionalised silicones and saturated C14-C22 straight chain fatty alcohols and mixtures thereof.

When present, the insoluble silicone conditioning agents are present at a level of from about 0.1 to 10%, preferably from about 0.1% to about 5%, more preferably from about 1% to about 3% by weight of composition. Suitable insoluble silicones include polyalkyl siloxanes, polyaryl siloxanes, polyalkylaryl siloxanes, polether siloxane copolymers, and mixtures thereof.

Other Additional Components

The compositions of the present invention typically further comprise a number of other components commonly utilized in hair care compositions such as shampoos, conditioners, styling aids and colorants which are well known to those skilled in the art such as for example thickeners and diluents. Additionally, a number of optional materials can be added to the compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol, benzoic acid, sodium benzoate and 2-phenoxyethanol; antioxidants such as sodium sulphite, hydroquinone, sodium bisulphite, sodium metabisulphite and thyoglycolic acid, sodium dithionite, erythrobic acid and other mercaptans; $H_2O_2$ stabilisers such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and >hydroxybenzoates; moisturising agents such as hyaluronic acid, chitin, and starch-grafted sodium polyacrylates as well as methyl cellulose, starch, higher fatty alcohols, paraffin oils, fatty acids and the like; solvents; anti-bacterial agents; low temperature phase modifiers such as ammonium ion sources (e.g. $NH_4Cl$); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; enzyme stabilisers such as water soluble sources of calcium or borate species; $TiO_2$ and $TiO_2$-coated mica; perfumes and perfume solubilizers; and zeolites and derivatives thereof and metal ion sequestrants such as poly-carboxylates, amino polycarboxylates, polyphosphonates, amino polyphosphonates etc. and water softening agents such as sodium citrate, inorganic peroxygen oxidising agents and enzymes.

Oxidizing Agent Composition

In addition, the aqueous oxidizing cream composition also comprises an oxidizing agent that will react with bleach the hair. Most often the aqueous oxidizing agent used is hydrogen peroxide, but other peroxides or oxidizing agents may be used such as calcium peroxide. Preferably the hydrogen peroxide concentration in the aqueous oxidizing agent composition ranges from about 10 to 40 volume, that is the amount of hydrogen peroxide that is present in the composition on a volume basis.

Additional suitable oxidizing agents (also referred to herein as "bleaching agents") include, for example, hydrogen peroxide sources, such as those described in detail in the herein incorporated Kirk Othmer's Encyclopedia of Chemical Technology, 4th Ed (1992, John Wiley & Sons), Vol. 4, pp. 271-300 "Bleaching Agents (Survey)." These hydrogen peroxide sources include the various forms of sodium perborate and sodium percarbonate, including various coated and modified forms of these compounds.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate, sodium percarbonate, sodium persulfate, and potassium persulfate are particularly preferred. Mixtures of any convenient hydrogen peroxide sources can also be used.

Compositions of the present invention may also comprise as the bleaching agent a chlorine-type bleaching material. Such agents are well known in the art and include for example sodium dichloroisocyanurate ("NaDCC").

In one aspect of the invention, the peroxygen bleach component in the composition is formulated with an activator (peracid precursor). The activator is present at levels of from about 0.01%, preferably from about 0.5%, more preferably from about 1% to about 15%, preferably to about 10%, more preferably to about 8%, by weight of the composition. A bleach activator as used herein is any compound which, when used in conjunction with a hydrogen peroxide, source leads to the in situ production of the peracid corresponding to the bleach activator. Various non-limiting examples of activators are disclosed in U.S. Pat. Nos. 5,576,282; 4,915,854 and 4,412,934. See also U.S. Pat. No. 4,634,551 for other typical bleaches and activators useful herein.

Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzene-sulphonate (NOBS), phenyl benzoate (PhBz), decanoyloxybenzenesulphonate ($C_{10}$—OBS), benzoylvalerolactam (BZVL), octanoyloxybenzenesulphonate ($C_8$—OBS), perhydrolyzable esters and mixtures thereof, most preferably benzoylcaprolactam and benzoylvalerolactam. Particularly preferred bleach activators in the pH range from about 8 to about 11 are those selected having an OBS or VL leaving group.

Preferred hydrophobic bleach activators include, but are not limited to, nonanoyloxybenzenesulphonate (NOBS); 4-[N-(nonanoyl) amino hexanoyloxy]-benzene sulfonate sodium salt (NACA-OBS), an example of which is described in U.S. Pat. No. 5,523,434; dodecanoyloxybenzenesulphonate (LOBS or $C_{12}$—OBS); 10-undecenoyloxybenzenesulfonate (UDOBS or $C_{11}$—OBS with unsaturation in the 10 position); and decanoyloxybenzoic acid (DOBA).

Preferred bleach activators are those described in U.S. Pat. No. 5,998,350 to Burns et al.; U.S. Pat. No. 5,698,504 to Christie et al.; U.S. Pat. No. 5,695,679 to Christie et al.; U.S. Pat. No. 5,686,401 to Willey et al.; U.S. Pat. No. 5,686,014 to Hartshorn et al.; U.S. Pat. No. 5,405,412 to Willey et al.; U.S. Pat. No. 5,405,413 to Willey et al.; U.S. Pat. No. 5,130,045 to Mitchel et al.; and U.S. Pat. No. 4,412,934 to Chung et al., and copending patent application Ser. No. 08/064,564, all of which are incorporated herein by reference.

Quaternary substituted bleach activators may also be included. The present compositions preferably comprise a quaternary substituted bleach activator (QSBA) or a quaternary substituted peracid (QSP, preferably a quaternary substituted percarboxylic acid or a quaternary substituted peroxyimidic acid); more preferably, the former. Preferred QSBA structures are further described in U.S. Pat. No. 5,686,015 to Willey et al.; U.S. Pat. No. 5,654,421 to Taylor et al.; U.S. Pat. No. 5,460,747 to Gosselink et al.; U.S. Pat. No. 5,584,888 to Miracle et al.; U.S. Pat. No. 5,578,136 to Taylor et al.; all of which are incorporated herein by reference.

Additional bleach activators useful herein are amide-substituted as described in U.S. Pat. Nos. 5,698,504; 5,695,679; and 5,686,014, each of which are cited herein above. Preferred examples of such bleach activators include: (6-octanamidocaproyl) oxybenzenesulfonate, (6-nonanamidocaproyl)oxybenzenesulfonate, (6-decanamidocaproyl) oxybenzenesulfonate and mixtures thereof.

Other useful activators are disclosed in U.S. Pat. Nos. 5,698,504; 5,695,679; and 5,686,014, each of which is cited herein above, and in U.S. Pat. No. 4,966,723 to Hodge et al. These activators include benzoxazin-type activators, such as a $C_6H_4$ ring to which is fused in the 1,2-positions a moiety —C(O)OC($R^1$)=N—.

Nitriles, such as acetonitriles and/or ammonium nitriles and other quaternary nitrogen containing nitriles, are another class of activators that are useful herein. Non-limiting examples of such nitrile bleach activators are described in U.S. Pat. Nos. 6,133,216; 3,986,972; 6,063,750; 6,017,464; 5,958,289; 5,877,315; 5,741,437; 5,739,327; 5,004,558; and in EP Nos. 790 244, 775 127, 1 017 773, 1 017 776; and in WO 99/14302, WO 99/14296, WO96/40661, all of which are incorporated herein by reference.

Depending on the activator and precise application, good bleaching results can be obtained from bleaching systems having an in-use pH of from about 6 to about 13, and preferably from about 9.0 to about 11.5. Typically, for example, activators with electron-withdrawing moieties are used for near-neutral or sub-neutral pH ranges. Alkalis and buffering agents can be used to secure such pH.

Acyl lactam activators, as described in U.S. Pat. Nos. 5,698,504; 5,695,679 and 5,686,014, each of which is cited herein above, may also be useful herein, especially the acyl caprolactams (see for example WO 94-28102 A) and acyl valerolactams (see U.S. Pat. No. 5,503,639 to Willey et al. incorporated herein by reference).

Organic peroxides, especially diacyl peroxides, may also be suitable for use. These are extensively illustrated in Kirk Othmer, Encyclopedia of Chemical Technology, Vol. 17, John Wiley and Sons, 1982 at pages 27-90 and especially at pages 63-72, all incorporated herein by reference. If a diacyl peroxide is used, it will preferably be one which exerts minimal adverse impact on fabric care, including color care.

The compositions and methods of the present invention can also optionally include metal-containing bleach catalysts, preferably manganese and cobalt-containing bleach catalysts.

One type of metal-containing bleach catalyst is a catalyst system comprising a transition metal cation of defined bleach catalytic activity (such as copper, iron, titanium, ruthenium tungsten, molybdenum, or manganese cations), an auxiliary metal cation having little or no bleach catalytic activity (such as zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 to Bragg.

If desired, the compositions herein can be catalyzed by means of a manganese compound. Such compounds and levels of use are well known in the art and include, for example, the manganese-based catalysts disclosed in U.S. Pat. Nos. 5,576,282; 5,246,621; 5,244,594; 5,194,416; and 5,114,606; and European Pat. App. Pub. Nos. 549,271 A1; 549,272 A1; 544,440 A2; and 544,490 A1. Preferred examples of these catalysts include $Mn^{IV}_2(u\text{-}O)_3(1,4,7\text{-trimethyl-}1,4,7\text{-triazacyclononane})_2(PF_6)_2$, $Mn^{III}_2(u\text{-}O)_1(u\text{-}OAc)_2(1,4,7\text{-trimethyl-}1,4,7\text{-triazacyclononane})_2(ClO_4)_2$, $Mn^{IV}_4(u\text{-}O)_6(1,4,7\text{-triazacyclononane})_4(ClO_4)_4$, $Mn^{III}Mn^{IV}_4(u\text{-}O)_1(u\text{-}OAc)_2\text{-}(1,4,7\text{-trimethyl-}1,4,7\text{-triazacyclononane})_2(ClO_4)_3$, $Mn^{IV}(1,4,7\text{-trimethyl-}1,4,7\text{-triazacyclononane})\text{-}(OCH_3)_3(PF_6)$, and mixtures thereof. Other metal-based bleach catalysts include those disclosed in U.S. Pat. Nos. 4,430,243 and 5,114,611. The use of manganese with various complex ligands to enhance bleaching is also reported in the following: U.S. Pat. Nos. 4,728,455; 5,284,944; 5,246,612; 5,256,779; 5,280,117; 5,274,147; 5,153,161; and 5,227,084.

Cobalt bleach catalysts useful herein are known, and are described, for example, in U.S. Pat. Nos. 5,597,936; 5,595,967; and 5,703,030; and M. L. Tobe, "Base Hydrolysis of Transition-Metal Complexes", *Adv. Inorg. Bioinorg. Mech.*, (1983), 2, pages 1-94. The most preferred cobalt catalyst useful herein are cobalt pentaamine acetate salts having the formula $[Co(NH_3)_5OAc] T_y$, wherein "OAc" represents an acetate moiety and "$T_y$" is an anion, and especially cobalt pentaamine acetate chloride, $[Co(NH_3)_5OAc]Cl_2$; as well as $[Co(NH_3)_5OAc](OAc)_2$; $[Co(NH_3)_5OAc](PF_6)_2$; $[Co(NH_3)_5OAc](SO_4)$; $[Co-(NH_3)_5OAc](BF_4)_2$; and $[Co(NH_3)_5OAc](NO_3)_2$ (herein "PAC").

These cobalt catalysts are readily prepared by known procedures, such as taught for example in U.S. Pat. Nos. 6,302,921; 6,287,580; 6,140,294; 5,597,936; 5,595,967; and 5,703,030; in the Tobe article and the references cited therein; and in U.S. Pat. No. 4,810,410; *J. Chem. Ed.* (1989), 66 (12), 1043-45; The Synthesis and Characterization of Inorganic Compounds, W. L. Jolly (Prentice-Hall; 1970), pp. 461-3; *Inorg. Chem.*, 18, 1497-1502 (1979); *Inorg. Chem.*, 21, 2881-2885 (1982); *Inorg. Chem.*, 18, 2023-2025 (1979); Inorg. Synthesis, 173-176 (1960); and *Journal of Physical Chemistry*, 56, 22-25 (1952).

Compositions herein may also suitably include as bleach catalyst a transition metal complex of a macropolycyclic rigid ligand. The amount used is a catalytically effective amount, suitably about 1 ppb or more, for example up to about 99.9%, more typically about 0.001 ppm or more, preferably from about 0.05 ppm to about 500 ppm (wherein "ppb" denotes parts per billion by weight and "ppm" denotes parts per million by weight).

Transition-metal bleach catalysts of macrocyclic rigid ligands which are suitable for use in the invention compositions can in general include known compounds non-limitingly illustrated by any of the following:

Dichloro-5,12-dimethyl-1,5,8,12-tetraazabicyclo[6.6.2] hexadecane Manganese(II)

Dichloro-5,12-diethyl-1,5,8,12-tetraazabicyclo[6.6.2] hexadecane Manganese(II)

Diaquo-5,12-dimethyl-1,5,8,12-tetraazabicyclo[6.6.2] hexadecaneManganese(II) Hexafluorophosphate Diaquo-5,12-diethyl-1,5,8,12-tetraazabicyclo[6.6.2]hexadecaneManganese(II) Hexafluorophosphate Aquo-hydroxy-5,12-dimethyl-1,5,8,12-tetraazabicyclo [6.6.2]hexadecane Manganese(III) Hexafluorophosphate Diaquo-5,12-dimethyl-1,5,8,12-tetraazabicyclo[6.6.2] hexadecaneManganese(II) Tetrafluoroborate Dichloro-5,12-dimethyl-1,5,8,12 tetraazabicyclo[6.6.2] hexadecane Manganese(III) Hexafluorophosphate Dichloro-5,12-diethyl-1,5,8,12-tetraazabicyclo[6.6.2] hexadecaneManganese(III) Hexafluorophosphate Dichloro-5,12-di-n-butyl-1,5,8,12-tetraaza bicyclo[6.6.2] hexadecane Manganese(II)

Dichloro-5,12-dibenzyl-1,5,8,12-tetraazabicyclo[6.6.2] hexadecaneManganese(II)

Dichloro-5-n-butyl-12-methyl-1,5,8,12-tetraaza-bicyclo [6.6.2]hexadecane Manganese(II)

Dichloro-5-n-octyl-12-methyl-1,5,8,12-tetraaza-bicyclo [6.6.2]hexadecane Manganese(II)

Dichloro-5-n-butyl-12-methyl-1,5,8,12-tetraaza-bicyclo [6.6.2]hexadecane Manganese(II).

The hair cream composition of the present invention may also include at least one bleaching agent. The bleaching agent may be selected from the group consisting of a Category 1 bleach, a Category 2 bleach, and mixtures thereof.

As a practical matter, and not by way of limitation, the compositions and methods herein can be adjusted to provide on the order of at least one part per hundred million of the active bleach catalyst species in the composition comprising a lipophilic fluid and a bleach system, and will preferably provide from about 0.01 ppm to about 25 ppm, more preferably from about 0.05 ppm to about 10 ppm, and most preferably from about 0.1 ppm to about 5 ppm, of the bleach catalyst species in the composition comprising a lipophilic fluid and a bleach system.

The compositions herein may comprise one or more bleach boosting compounds. Bleach boosting compounds provide increased bleaching effectiveness in lower temperature applications. The bleach boosters act in conjunction with conventional peroxygen bleaching sources to provide increased bleaching effectiveness. This is normally accomplished through in situ formation of an active oxygen transfer agent such as a dioxirane, an oxaziridine, or an oxaziridinium. Alternatively, preformed dioxiranes, oxaziridines and oxaziridiniums may be used.

Among suitable bleach boosting compounds for use in accordance with the present invention are cationic imines, zwitterionic imines, anionic imines and/or polyionic imines having a net charge of from about +3 to about −3, and mixtures thereof. These imine bleach boosting compounds of the present invention include those of the general structure:

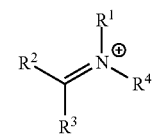

[A]

where $R^1$-$R^4$ may be a hydrogen or an unsubstituted or substituted radical selected from the group consisting of phenyl, aryl, heterocyclic ring, alkyl and cycloalkyl radicals.

Among preferred bleach boosting compounds are zwitterionic bleach boosters, which are described in U.S. Pat. Nos. 5,576,282 and 5,718,614. Other bleach boosting compounds include cationic bleach boosters described in U.S. Pat. Nos. 5,360,569; 5,442,066; 5,478,357; 5,370,826; 5,482,515; 5,550,256; and WO 95/13351, WO 95/13352, and WO 95/13353.

Peroxygen sources are well-known in the art and the peroxygen source that could be employed in the present invention may comprise any of these well known sources, including peroxygen compounds as well as compounds, which under consumer use conditions, provide an effective amount of peroxygen in situ. The peroxygen source may include a hydrogen peroxide source, the in situ formation of a peracid anion through the reaction of a hydrogen peroxide source and a bleach activator, preformed peracid compounds or mixtures of suitable peroxygen sources. Of course, one of ordinary skill in the art will recognize that other sources of peroxygen may be employed without departing from the scope of the invention. The bleach boosting compounds, when present, are preferably employed in conjunction with a peroxygen source in the bleaching systems of the present invention.

Also suitable as bleaching agents are preformed peracids. The preformed peracid compound as used herein is any convenient compound which is stable and which under consumer use conditions provides an effective amount of peracid or peracid anion. The preformed peracid compound may be selected from the group consisting of percarboxylic acids and salts, percarbonic acids and salts, perimidic acids and salts, peroxymonosulfuric acids and salts, and mixtures thereof. Examples of these compounds are described in U.S. Pat. No. 5,576,282 to Miracle et al.

One class of suitable organic peroxycarboxylic acids have the general formula:

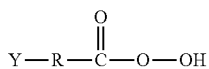

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted peracid has the general formula:

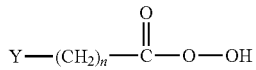

wherein Y can be, for example, H, $CH_3$, $CH_2Cl$, C(O)OH, or C(O)OOH; and n is an integer from 0 to 20. When the organic peroxycarboxylic acid is aromatic, the unsubstituted peracid has the general formula:

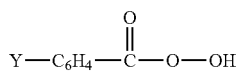

wherein Y can be, for example, hydrogen, alkyl, alkylhalogen, halogen, C(O)OH or C(O)OOH.

Typical monoperoxy acids useful herein include alkyl and aryl peroxyacids such as:
 (i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);
 (ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);
 (iii) amidoperoxyacids, e.g. mononoylamide of either peroxysuccinic acid (NAPSA) or of peroxyadipic acid (NAPAA).

Typical diperoxyacids useful herein include alkyl diperoxyacids and aryldiperoxyacids, such as:
 (i) 1,12-diperoxydodecanedioic acid;
 (ii) 1,9-diperoxyazelaic acid;
 (iii) diperoxybrassylic acid; diperoxysebacic acid and diperoxyisophthalic acid;
 (iv) 2-decyldiperoxybutane-1,4-dioic acid;
 (v) 4,4'-sulfonylbisperoxybenzoic acid.

Such bleaching agents are disclosed in U.S. Pat. No. 4,483,781 to Hartman and U.S. Pat. No. 4,634,551 to Burns et al.; European Patent Application 0,133,354 to Banks et al.; and U.S. Pat. No. 4,412,934 to Chung et al. Sources also include 6-nonylamino-6-oxoperoxycaproic acid as described in U.S. Pat. No. 4,634,551 to Burns et al. Persulfate compounds such as for example OXONE, manufactured commercially by E.I. DuPont de Nemours of Wilmington, Del. can also be employed as a suitable source of peroxymonosulfuric acid. PAP is disclosed in, for example, U.S. Pat. Nos. 5,487,818; 5,310,934; 5,246,620; 5,279,757 and 5,132,431.

Photobleaches may also be suitable for use in the compositions of the present invention and include, but are not limited to, the photobleaches described in U.S. Pat. Nos. 4,217,105 and 5,916,481.

Enzymatic systems may be used as bleaching agents. The hydrogen peroxide may also be present by adding an enzymatic system (i.e. an enzyme and a substrate therefore) which is capable of generating hydrogen peroxide. Such enzymatic systems are disclosed in EP Patent Application 91202655.6 filed Oct. 9, 1991.

The present invention compositions and methods may utilize alternative bleach systems such as ozone, chlorine dioxide and the like. Bleaching with ozone may be accomplished by introducing ozone-containing gas having ozone content from about 20 to about 300 $g/m^3$ into the solution that is to contact the hair. The gas:liquid ratio in the solution should be maintained from about 1:2.5 to about 1:6. U.S. Pat. No. 5,346,588 describes a process for the utilization of ozone as an alternative to conventional bleach systems and is herein incorporated by reference.

Colorants

The coloring compositions of the present disclosure may optional contain one or more colorant other than polymeric colorants. These color compound can be chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2- chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(.beta.,.gamma.-dihydroxypropyl)-para-phenylenediamine, N-(4'-aminophenyl)-para-phenylenediamine, N-phenyl-para-phenylenediamine, 2-.beta-hydroxyethyloxy-para-phenylenediamine, 2-beta.-acetylaminoethyloxy-para-phenylenediamine, N-(.beta.-methoxyethyl)-para-phenylenediamine, 4-aminophenylpyrrolidine, 2-thienyl-para-phenylenediamine, 2-.beta.-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-.beta.-hydroxyethyl-para-phenylenediamine, 2-.beta.-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(.beta.-hydroxyethyl)-para-phenylenediamine, 2-chloro-para-phenylenediamine and 2-beta-acetylaminoethyloxy-para-phenylenediamine, and the addition salts thereof with an acid, are particularly preferred.

Among the bis(phenyl)alkylenediamines that may be mentioned, for example, are N,N'-bis(.beta.-hydroxyethyl)-N,N'-bis(4'-aminophenyl)-1,3-diaminopropano-1, N,N'-bis(.beta.-hydroxyethyl)-N,N'-bis(4'-aminophenyl)ethylenediamine, N,N'-bis(4-aminophenyl)tetramethylenediamine, N,N'-bis(.beta.-hydroxyethyl)-N,N'-bis(4-aminophenyl)tetramethylenediamin-e, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(.beta.-hydroxyethylaminomethyl)phenol and 4-amino-2-fluorophenol, and the addition salts thereof with an acid. Among the ortho-aminophenols that may be mentioned, for example, are 2-aminophenol, 2-amino-5-methylphenol, 2-amino-6-methylphenol and 5-acetamido-2-aminophenol, and the addition salts thereof. Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:
(a) one (di)(Ci-$C_6$)(alkyl)amino group wherein said alkyl group can be substituted by at least one hydroxy, amino, imidazolium group;
(b) one heterocycloalkyl group containing from 5 to 7 members chain, and from 1 to 3 heteroatoms, potentially cationic, potentially substituted by one or more (Ci-$C_6$-alkyl, such as di(C1-C4)alkylpiperazinium; or
(c) one (Ci-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists. Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1 H,5H- pyrazolo[1,2-a]pyrazol-~1-one, 2-amino-3-dimethylamino-6,7-dihydro-1 H,5H-pyrazolo[1,2-a]pyrazol-1-one, 2,3-diamino-5,6,7,8-tetrahydro-1 H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1 H,5H-pyrazolo[1,2-a]pyrazol-1-o-ne. 2,3-Diamino-6,7-dihydro-1 H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1 H,5H-pyrazolo[1,2-a]pyrazol-1-one and/or a salt thereof will preferentially be used as heterocyclic bases.

Compositions according to the present disclosure may optionally comprise one or more couplers advantageously chosen from those conventionally used in the dyeing or coloring of keratin fibers. Among these couplers, mention may be made especially of meta-phenylenediamines, meta-aminophenols, meta-diphenols, naphthalene-based couplers and heterocyclic couplers, and also the addition salts thereof. Mention may be made, for example, of 2-methyl-5-aminophenol, 5-N-(.beta.-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(.beta.-hydroxyethyloxy)benzene, 2-amino-4-(.beta.-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-.beta.-hydroxyethylamino-3,4-methylene-dioxybenzene, .alpha.-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(.beta-hydroxyethyl)amino-3,4-methylene-dioxybenzene, 2,6-bis(J-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates. The oxidation base(s) each advantageously represent from 0.001% to 10% by weight relative to the total weight of the composition, and preferably from 0.005% to 5% by weight relative to the total weight of the compositions of the present disclosure. The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may comprise b) one or more synthetic or natural direct dyes or pigment. Suitable dyes or pigment includes but not limited to those listed in Annex IV in regulation (EC) No 1223/2009 of the European parliament and of the council. Examples of suitable direct dyes that may be mentioned include azo direct dyes; (poly)methine dyes such as cyanins, hemicyanins and styryls; carbonyl dyes; azine dyes; nitro(hetero)aryl dyes; tri(hetero)aryl methane dyes; porphyrin dyes; phthalocyanin dyes, and natural direct dyes, alone or as mixtures. Many direct dyes are cationic direct dyes. Mention may be made of the hydrazono cationic dyes, the azo cationic dyes, and the diazo cationic dyes. Particular examples include Basic Red 51, Basic Yellow 87 and Basic Orange 31 or derivatives thereof. Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices, or extracts may also be used. When they are present, the direct dye(s) more particularly represent from 0.001% to 10% by weight and preferably from 0.005% to 5% by weight of the total weight of the compositions of the present disclosure.

Alkalizing Agents

The oxidative hair cream composition may have a pH that is alkaline. Exemplary pH's include 7, 8, 9, 10, 11, 12, 13 or 14. In some embodiments, the pH of the composition may range from about 7, 8, or 9 to about 9, 10, 11 or 12. The alkalinity of the oxidative hair cream composition may be derived from one or more alkalizing agents. In some embodiments, the alkalizing agent may ammonia or an ammonia gas-generating compound and/or an amine or ammonium-based compound in amounts sufficient to make such compositions alkaline. In further embodiments, the alkalizing agent may be selected from alkanolamines, such as monoethanolamine (MEA) and isopropanolamine. Alkalinity may be derived from ammonium compounds as well (e.g., $NH_4OH$). One or more alkalizing agents may be present in amounts ranging from greater than about 0, or from 1, 2, 3, 4, 5, 10 to about 5, 10, 13, 15, 18, 20, 25 or 30% by weight of the total composition.

The oxidative hair cream compositions may be in the form of a cream, an aqueous solution, a uniform dispersion, or a suspension of surfactant, or even a liquid. Such compositions will be acceptably phase stable and will typically have a viscosity which ranges from about 1 to 1,000,000 cps, more preferably from about 10 to 100,000, most preferably from 100 to 20,000 cps, even more preferably from 1000 to 10000 cps. For purposes of this invention, viscosity is measured with a Brookfield LVDV-II+ viscometer apparatus at room temperature at 1 rpm with corresponding cup and spindle.

The oxidative hair cream composition of the present invention also contains at least one coloring agent that the thiophene azo chromophore. Generally, the thiophene azo colorant may be characterized by having an absorbance in the range of between about 400 nanometers and about 700 nanometers, as measured by UV-vis spectroscopy. In one aspect of the invention, the thiophene azo colorant has a maximum absorbance in the range from 500 nanometers to 650 nanometers, or a maximum absorbance in the range from 540 nanometers to 700 nanometers, or even in the range from 540 nanometers to 630 nanometers.

As a function of its manufacturing process, the thiophene azo colorant has a molecular weight that is typically represented as a molecular weight distribution. Accordingly, the molecular weight of the thiophene azo colorant is generally reported as an average molecular weight, as determined by its molecular weight distribution.

In one aspect, the thiophene azo colorant may be a neutral or an uncharged molecule. In a further aspect, the colorant may be nonionic, anionic, or cationic. The thiophene azo colorant may contain a chromophore that has both positive and negative charges. Further, the thiophene azo colorant may contain a chromophore that is zwitterionic or ampho-teric.

The thiophene azo colorant may be alkoxylated. Alkoxylation is carried out by procedures well-known to those skilled in the art (see, for example, U.S. Pat. Nos. 4,137,243; 5,082,938; 5,135,972; 5,591,833; 6,593,483; 7,587,857; 9,056,963; and 9,068,081).

In one aspect of the invention, the oxidative hair cream composition contains a thiophene azo colorant according to Formula I:

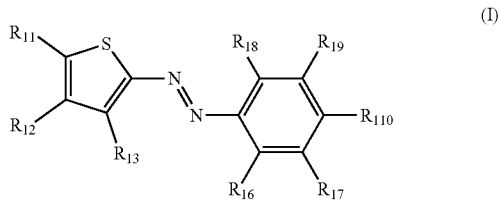

(I)

wherein each $R_{11}$ to $R_{110}$ group is independently selected from the group consisting of hydrogen, deuterium and $R^v$; each $R^v$ is independently selected from the group consisting of halogens, nitro, nitrile, alkyl, substituted alkyl, alkenyl, substituted alkenyl, aryl, substituted aryl, alkynyl, substituted alkynyl, $-(CH_2)_n-O-R^x$, $-(CH_2)_n-NR^xR^y$, $-CR^xR^yR^z-C(O)R^x$, $-C(O)OR^x$, $-C(O)O^-$, $-C(O)NR^xR^y$, $-OC(O)R^x$, $-OC(O)OR^x$, $-OC(O)NR^xR^y$, $-S(O)_2R^x$, $-S(O)_2OR^x$, $-S(O)_2O^-$, $-S(O)_2NR^xR^y$, $-NR^xC(O)R^y$, $-NR^xC(O)OR^y$, $-NR^xC(O)SR^y$, $-NR^xC(O)NR^yR^x$, $-OR^x$, $-NR^xR^y$, $-P(O)_2R^x$, $-P(O)(OR^x)_2$, $-P(O)(OR^x)O^-$, and $-P(O)(O^-)_2$; wherein the index n is an integer from 0 to 4, preferably from 0 to 1, most preferably 0; preferably at least one of the $R_{11}$, $R_{12}$, and $R_{13}$ is an electro-withdrawing groups select from halogens, nitro, nitrile, nitroso, $-C(O)R^x$, $-C(O)OR^x$, $-C(O)NR^xR^y$, $-OC(O)R^x$, $-OC(O)OR^x$, $-OC(O)NR^xR^y$, $-S(O)_2R^x$, $-S(O)_2OR^x$, $-P(O)_2R^x$, and $-P(O)(OR^x)_2$ groups, preferably $R_{16}$, $R_{17}$, $R_{18}$, $R_{19}$, $R_{110}$ are independently selected from hydrogen, halogens, methyl group, ethyl groups, propyl groups, isopropyl group, n-butyl group, isobutyl groups, 2-butyl groups, tert-butyl groups, $-(CH_2)_n-O-R^x$, $-(CH_2)_n-NR^xR^y$, $-OR^x$, and $-NR^xR^y$, and at least one of $R_{16}$, $R_{17}$, $R_{18}$, $R_{19}$, $R_{110}$ is $-OR^x$, or $-NR^xR^y$. $R^x$, $R^y$ and $R^z$ are independently selected from the group consisting of hydrogen, alkyl, substituted alkyl, alkenyl, substituted alkenyl, aryl, substituted aryl, alkynyl, substituted alkynyl, and $R^u$; $R^u$ is an organic group composed of one or more organic monomers with said monomer molecular weights ranging from 28 to 500, preferably from 43 to 350, even more preferably from 43 to 250. Two or more $R_{16}$, $R_{17}$, $R_{18}$, $R_{19}$, $R_{110}$ can be connected to each other through covalent bonds to form a ring structure. Combined with a benzene ring, the ring may form structures including but not limited to naphthalene, tetrahydroquinoline, tetrahydroisoquinoline, indoline, and isoindoline. This ring structure may be further substituted by one or more $R_{16}$ groups. Two of the $R^x$, $R^y$, or $R^z$, when attached to the same carbon or nitrogen atom, may also connect to form the ring structure. Exemplary ring structures include but are not limited to piperazine, piperidine, and pyrrolidine. This ring structure may be further substituted by one or more $R_{16}$ groups.

In one aspect of the invention, the oxidative hair cream composition contains a thiophene azo colorant according to Formula V:

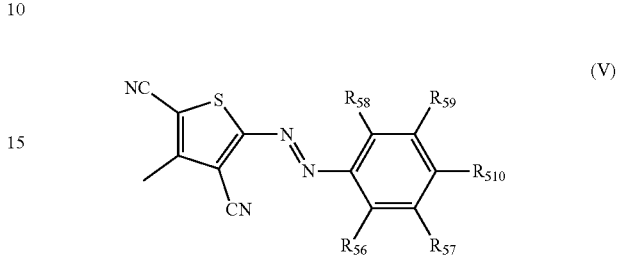

(V)

wherein $R_{56}$, $R_{57}$, $R_{58}$, $R_{59}$, and $R_{510}$ groups are independently selected from hydrogen, halogens, alkyl, substituted alkyl, alkenyl, substituted alkenyl, aryl, substituted aryl, alkynyl, substituted alkynyl, $-(CH_2)_n-O-R^x$, $-(CH_2)_n-NR^xR^y$, $-CR^xR^yR^z$, $-C(O)O-$, $-NR^xC(O)R^y$, $-NR^xC(O)OR^y$, $-NR^xC(O)SR^y$, $-NR^xC(O)NR^xR^y$, $-OR^x$, $-NR^xR^y$, $-P(O)(OR^x)O^-$, and $-P(O)(O^-)_2$; Two of more $R_{56}$, $R_{57}$, $R_{58}$, $R_{59}$, $R_{510}$ can be connected to each other through covalent bonds to form a ring structure. $R^x$, $R^y$ and $R^z$ are independently selected from the group consisting of hydrogen, alkyl, substituted alkyl, alkenyl, substituted alkenyl, aryl, substituted aryl, alkynyl, substituted alkynyl, and $R^u$; $R^u$ is an organic group composed of one or more organic monomers with said monomer molecular weights ranging from 28 to 500, preferably from 43 to 350, even more preferably from 43 to 250. Two or more $R_{56}$, $R_{57}$, $R_{58}$, $R_{59}$, $R_{510}$ can be connected to each other through covalent bonds to form a ring structure. When combined with a benzene ring, the ring may form structures including but not limited to naphthalene, tetrahydroquinoline, tetrahydroisoquinoline, indoline, and isoindoline. This ring structure may further be substituted by one or more groups like $R_{56}$. Two of the $R^x$, $R^y$, or $R^z$, when attached to the same carbon or nitrogen group, may also connect to form the ring structure. Exemplary ring structures include but are not limited to piperazine, piperidine, and pyrrolidine. This ring structure may be further substituted by one or more $R_{56}$ groups.

In yet another aspect of the invention, the oxidative hair cream composition contains a thiophene azo colorant according to Formula IV:

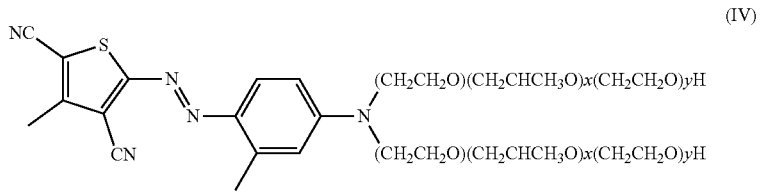

(IV)

wherein each x and y are independently integers from 0 to 20.

It is also contemplated to be within the scope of the present invention that other colorants may be combined with the thiophene azo colorant to form the coloring agent portion of the oxidative hair cream composition. For example, a colorant selected from one or more of the following classes may be suitable: acid dyes, basic dyes, direct dyes, solvent dyes, vat dyes, mordant dyes, indigoid dyes, reactive dyes, disperse dyes, sulfur dyes, fluorescent dyes; pigments, both organic and inorganic; natural colorants; and the like.

The oxidative hair cream composition of the present invention is prepared by combining at least one oxidizing agent with at least one thiophene azo colorant. The oxidative hair cream composition thus formed may be a substantially homogenous mixture.

A method for preparing the oxidative hair cream composition of the present invention is comprised of the following steps:
 (a) providing at least one oxidizing agent;
 (b) providing at least one thiophene azo colorant; and
 (c) combining the at least one oxidizing agent and the at least one thiophene azo colorant to form a thiophene azo colorant-containing oxidative hair cream.

A method for applying color to hair according to the present invention is comprised of the following steps:
 (a) providing a thiophene azo colorant-containing oxidative hair cream;
 (b) applying the thiophene azo colorant-containing oxidative hair cream to hair;
 (c) allowing the hair cream to contact the hair for a period of time; and
 (d) removing the hair cream from the hair.

A method for bleaching and applying color to hair according to the present invention is comprised of the following steps:
 (a) providing a thiophene azo colorant-containing oxidative hair cream;
 (b) applying the thiophene azo colorant-containing oxidative hair cream to hair;
 (c) allowing the hair cream to contact the hair for a period of time; and
 (d) removing the hair cream from the hair.

The oxidative hair cream composition may be allowed to contact the hair for a period of time in the range from 10 seconds to 1 hour, or in the range from 30 seconds to 45 minutes, or in the range from 1 minute to 30 minutes, or in the range from 3 minutes to 15 minutes. The hair may be wet with water prior to application of the hair cream, or the hair may be dry when the hair cream is applied to the hair.

The oxidative hair cream may be permanent (e.g. 80% of original color intensity is still visible after 20 wash cycles), semi-permanent (e.g. 80% of original color intensity is visible up to, but not subsequent to, 20 wash cycles), or temporary (e.g. 80% of original color intensity is visible up to, but not subsequent to, 5 wash cycles). The permanence of the hair color on the hair may depend on the specific thiophene azo colorant included in the hair cream and/or the amount of thiophene azo colorant included in the hair cream. For example, increasing the amount of thiophene azo colorant in the hair cream may result in the color lasting longer on the hair. In contrast, including less thiophene azo colorant in the hair cream may result in the color lasting less time on the hair. Also, the amount of time the oxidative hair cream remains in contact with the hair during the coloring process may affect amount of color, depth of color and/or shade, and the permanence of the hair color on the hair. For instance, leaving the hair cream on the hair for a longer period of time during the hair coloring process may result in a greater depth of shade and/or color and color that lasts longer on the hair.

In one aspect of the invention, the amount of thiophene azo colorant in the hair cream is in the range from 0.0001%-10% or in the range from 0.1%-5%.

In one aspect of the invention, the molecular weight of thiophene azo colorant in the hair cream is in the range from 100-10000 or in the range from 200-5000 or in the range from 300 to 2000.

At least one thiophene azo colorant as described herein may be added to an oxidative hair cream composition for use in coloring hair. As a result, the invention also encompasses hair (or a keratin-containing material) containing at least one thiophene azo colorant. The invention further encompasses a process for bleaching and/or coloring hair (or a keratin-containing material) that includes the steps of providing hair, applying and/or depositing an oxidative hair cream composition as described herein to the hair, allowing the oxidative hair cream composition to contact the hair for a period of time, and further agitating, rinsing, and/or drying the thus treated hair.

There are typically two components in these types of oxidative systems. One component contains an oxidative species (such as hydrogen peroxide). The second component contains other species, typically designed to raise pH, but could also contain other oxidative species such as persulfates. In one aspect of the invention, the two components are mixed together before applying to hair. The initial application includes the thiophene azo colorant in the hydrogen peroxide cream, not in the second component. However, it is conceivable to put the thiophene azo colorant in the second component instead.

Thus, in one embodiment, at least one thiophene azo colorant is mixed into an oxidizer containing cream. Immediately before use, the thiophene azo colorant/hydrogen peroxide containing cream is mixed with at least one other component that raises the pH a sufficient amount to activate the hydrogen peroxide. In an alternative embodiment, the thiophene azo colorant may be added to the second component. In this instance, the second component is added to the uncolored hydrogen peroxide cream immediately before use.

While the invention described herein has been directed mainly to oxidative hair creams containing thiophene azo colorants, it is not limited to only those compositions. The oxidative hair cream may contain a combination of thiophene azo colorant and another coloring agent. Other coloring agents include, for example, dyes, pigments, and combinations thereof.

Suitable dyes include small molecule dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. Examples of small molecule dyes include those selected from the group consisting of Colour Index (Society of Dyers and Colourists, Bradford, UK) numbers Direct Violet 9, Direct Violet 35, Direct Violet 48, Direct Violet 51, Direct Violet 66, Direct Violet 99, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Violet 50, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159, small molecule dyes selected from the group consisting of Colour Index (Society of Dyers and Colourists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In one aspect of the invention, the components of the oxidative hair care composition may be prepared by combining the components in any convenient order and by mixing, e.g., agitating, the resulting component combination to form a phase stable semi-liquid (i.e. cream) composition. In another process for preparing such compositions, a liquid matrix is formed containing at least a major proportion, and preferably substantially all, of the liquid components, with the liquid components being thoroughly admixed by imparting shear agitation to this liquid combination. For example, rapid stirring with a mechanical stirrer may usefully be employed. While shear agitation is maintained, substantially all of any solid form ingredients can be added. Agitation of the mixture is continued, and if necessary, can be increased at this point to form a solution or a uniform dispersion of insoluble solid phase particulates within the liquid phase. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

The oxidative hair cream of the present invention may be combined with other molecules, compounds, and/or agents useful for applying the oxidative hair cream to hair and/or for enhancing color performance. Other molecules, compounds and/or agents include, for example, surfactants, solvents, preservatives, antimicrobial agents, antibacterial agents, perfumes, and the like, and combinations thereof.

The oxidative hair cream compositions of the present invention may also include any number of additional optional ingredients. These include conventional hair colorant composition components such as . . . alkalizing agents (such as ammonia), sources of alkalinity (such as silicate and/or carbonate salts), humectants, conditioning agents, thickening agents, non-tinting dyes, detersive builders, enzymes, enzyme stabilizers, suds suppressors, pH adjusting agents, chelating agents, smectite clays, solvents, hydrotropes and phase stabilizers, structuring agents, opacifying agents, perfumes and coloring agents. The various optional oxidative hair cream composition ingredients, if present in the compositions herein, should be utilized at concentrations conventionally employed to bring about their desired contribution to the composition or the hair bleaching and/or coloring process. Frequently, the total amount of such optional oxidative hair cream composition ingredients can range from about 0.01% to about 50%, more preferably from about 0.1% to about 30%, by weight of the composition.

Examples

Several colorants were tested for stability and coloring performance in a commercially available oxidative hair cream. Each sample was added to Fanola 40 Vol Perfumed Cream Developer (available from Fanola of Italy), which contained about 12% hydrogen peroxide. Each sample was mixed using a SpeedMixer at 1500 rpm until a visually uniform mixture was obtained, at minimum 90 seconds. (SpeedMixer from Inc., Landrum, S.C.). The amount of color contained in each sample was adjusted so that each sample exhibited the same color strength. The maximum absorbance of the colored cream was 0.67 when measured with 1 cm path length at concentration of 10 gram/liter in methanol. After mixing, the samples were stored first at room temperature for 7 days and then moved to a 40° C. oven. The stability of color was evaluated by the room temperature equivalent days it takes to reach 50% loss of color based the original measured color in the cream at time zero as measured by UV-VIS. Loss of color is decoloration due to chemical changes in colorant from the oxidative cream ingredients including peroxide.

The room temperature equivalent days was calculated by the following equation:

Room temperature equivalent days=Days stored at room temperature+Days stored at 40° C.*3.48

Using the room temperature equivalent days for the color to degrade to 50%, a rating was generated according to Table 1. A rating of "1" means the most stable, while a rating of "5" is the least stable.

TABLE 1

Rating Scale for Stability of Oxidative Hair Cream Containing Colorant

| Rating | Room temperature equivalent days to 50% |
|---|---|
| 1 | More than 300 days |
| 2 | From 150 to 300 days |
| 3 | From 50 to 150 days |
| 4 | From 20 to 50 days |
| 5 | Less than 20 days |

The inventive colorants and stability test results are shown in Table 2A. The comparative colorants and stability test results are shown in Table 2B.

TABLE 2A

| Sample Number and Product Name | Structure | Rating |
|---|---|---|
| Example 1 | NC, S, with azo linkage to phenyl bearing N[(CH₂CH₂O)(CH₂CHCH₃O)₇(CH₂CH₂O)₄H]₂, methyl, and CN substituents | 1 |
| Example 2 | NC, S, with azo linkage to phenyl bearing N(CH₂CH₂OH)₂, methyl, and CN substituents | Not Tested |

TABLE 2B

| Sample Number and Product Name | Description | Rating |
|---|---|---|
| Comparative Example 1 Violet | Polymeric triarylmethane dye with poly(ethylene oxide) with 16-24 repeating units | 5 |
| Comparative Example 2 Violet | Polymeric triarylmethane dye with poly(ethylene oxide) with 8-12 repeating units | 5 |
| Comparative Example 3 Blue | Polymeric triarylmethane dye with poly(ethylene oxide) with 8-12 repeating units | 4 |
| Comparative Example 4 Cyan | Polymeric triarylmethane dye with poly(ethylene oxide) with 16-24 repeating units | 5 |
| Comparative Example 5 Blue | Polymeric triarylmethane dye with poly(ethylene oxide) with 8-12 repeating units | 5 |
| Comparative Example 6 Red | Polymeric cyanine dye with poly(ethylene oxide) with 16-20 repeating units. | 5 |
| Comparative Example 7 Yellow | Polymeric methine dye with poly(ethylene oxide) with 16-20 repeating units. | 5 |
| Comparative Example 8 Blue | Polymeric anthraquinone dye with poly(ethylene oxide) with 3-10 repeating unites. | 5 |
| Comparative Example 9 Violet | Polymeric anthraquinone dye with poly(ethylene oxide) with 8-15 repeating unites. | 3 |
| Comparative Example 10 External D&C Violet 2 | 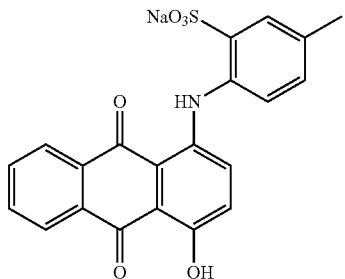 | 1 |

TABLE 2B-continued

Comparative Colorants

| Sample Number and Product Name | Description | Rating |
|---|---|---|
| Comparative Example 11 Solvent Violet 13 | [Structure of 1-(p-tolylamino)-4-hydroxyanthraquinone] | 1 |

Test results demonstrate that all polymeric triarylmethane dye were not stable (Comparative Examples 1-5). Other polymeric dye classes such as cyanine (Comparative Examples 6), methine (Comparative Examples 7), and anthraquinone (Comparative Examples 8 and 9) were not stable, either. The monomeric anthraquinone dyes, such as External D&C Violet 2 (Comparative Example 10) and Solvent Violet 13 (Comparative Example 11), were found to be difficult to blend into the cream but have better stability in comparison to their polymeric counterparts (Comparative Examples 8 and 9).

Coloring Performance Evaluation

Materials:

Blonde Hair (lightly bleached dark hair)), cut to 3 cm wide, 20 cm long

Fanola Violet Bleach Powder

Fanola 40 Vol. (12% peroxide) oxidative cream

Procedure:

The hair was weighed first in order to calculate the amount of cream needed (4 grams of cream per gram of hair). Color and oxidative cream developer were mixed as described above. The mixtures were checked and remixed when necessary to ensure the color was fully homogenous. Fanola Violet Bleach Powder (available from Fanola of Italy) was weighed into a small weigh boat (two parts cream to one part bleach powder). The appropriate amount of oxidative cream was added to the bleach powder. Using the wooden end of a cotton-tipped applicator, the bleach/cream was stirred until fully mixed. The bleach/cream mixture was transferred to a large weigh boat with the hair sample. The mixture was spread all over the hair and worked into the hair with fingertips until the mixture was fully incorporated evenly throughout the hair. The bleach was allowed to sit on the hair for 15 minutes and then the hair sample was rinsed thoroughly with lukewarm water, combed, and dried in the oven at 60° C. for 45 minutes. The color of hair was measured using the X-Rite Color-i with a 6 mm aperture, with D-65 light source. The hair was twisted tight and pressed to the aperture while taking the measurement. An average of 6-8 measurements was used.

The CIE WI is a good indicator for how well the hair was lightened. The initial hair had a whiteness index (WI) of −76.6 due to its yellow color. After treatment, the WI values increased, indicating the hair was lightened. The differences of the WI between treated hair and initial hair, ΔWI, were recorded. Larger ΔWI indicate better lightening of the hair.

The WI and ΔWI values of the initial hair, bleach control (no dye), and bleach composition containing Example 1, Example 2 and Comparative Example 10 (External D&C Violet 2) are shown in Table 3. The bleach composition with Example 1 and Example 2 provided better lightening than the bleach control and bleach with Comparative Example 10.

TABLE 3

Color Evaluation

| Sample | WI Value | ΔWI Value |
|---|---|---|
| Initial Hair | −76.6 | n/a |
| Oxidative Hair Cream Control | −60.0 | 16.6 |
| Oxidative Hair Cream with Example 1 | −46.1 | 30.5 |
| Oxidative Hair Cream with Example 2 | −47.1 | 29.5 |
| Oxidative Hair Cream with Comparative Example 12 | −55.7 | 20.9 |

When dark hair is bleached, the melanin pigments are destroyed which leads to the visual enhancement of the red pigments and the casting of an undesirable warm reddish orange or "brassy" tone to the bleached hair. This brassy tone is typically corrected by the post bleaching application of a violet or blue dye. The blue or violet is complementary to the orange and yellow brassy tones and effectively neutralizes this tone. This dye can be delivered in a shampoo, conditioner, mask, hair cream, or something similar. It would be preferable to add a violet or blue colorant into the bleaching cream so that the brassy tones are directly neutralized during the bleaching process and so no additional color treatment is necessary. The challenge is that the oxidative cream is generally an aggressive condition which will decolor many colorants. The present invention relates to a particular subset of dyes that are both stable in the oxidative cream upon storage and also the correct color for neutralizing the brassy tones.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

We claim:

1. An oxidative hair cream composition, wherein the composition comprises: (a) at least one thiophene azo colorant according to Formula I:

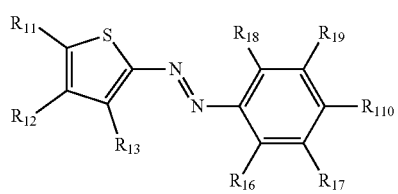

(I)

wherein at least one of the $R_{11}$, $R_{12}$, and $R_{13}$ is an electro-withdrawing groups selected from halogens, nitro, nitrile, nitroso, —C(O)$R^x$, —C(O)O$R^y$, —C(O)NR$^x$R$^y$, —OC(O)$R^x$, —OC(O)O$R^x$, —OC(O)NR$^x$R$^y$, —S(O)$_2$R$^x$, —S(O)$_2$OR$^x$, —P(O)$_2$R$^x$, and —P(O)(OR$^x$)$_2$ groups;

wherein $R_{16}$, $R_{17}$, $R_{18}$ and $R_{19}$ are independently selected from hydrogen, halogens, methyl group, ethyl groups, propyl groups, isopropyl group, n-butyl group, isobutyl groups, 2-butyl groups, tert-butyl groups, —(CH$_2$)$_n$—O—R$^x$, —(CH$_2$)—NR$^x$R$^y$, —OR$^x$, and —NR$^x$R$^y$, and at least one of $R_{16}$, $R_{17}$, $R_{18}$, $R_{19}$, $R_{110}$ is —OR$^x$, or —NR$^x$R$^y$;

wherein two or more of $R_{16}$, $R_{17}$, $R_{18}$, $R_{19}$, $R_{110}$ are connected to each other through covalent bonds to form a ring structure fused with the benzene ring in Formula I;

wherein $R_{110}$ is selected from the group consisting of hydrogen, deuterium and R$^v$;

each R$^v$ is independently selected from the group consisting of halogens, nitro, nitrile, alkyl, substituted alkyl, alkenyl, substituted alkenyl, aryl, substituted aryl, alkynyl, substituted alkynyl, —(CH$_2$)$_n$—O—R$^x$, —(CH$_2$)—NR$^x$R$^y$, —C(O)R$^x$, —C(O)OR$^x$, —C(O)O$^-$, —C(O)NR$^x$R$^y$, —OC(O)R$^x$, —OC(O)OR$^x$, —OC(O)NR$^x$R$^y$, —S(O)$_2$R$^x$, —S(O)$_2$OR$^x$, —S(O)$_2$O$^-$, —S(O)$_2$NR$^x$R$^y$, —NR$^x$C(O)R$^y$, —NR$^x$C(O)OR$^y$, —NR$^x$C(O)SR$^y$, —NR$^x$C(O)NR$^y$R$^z$, —OR$^x$, —NR$^x$R$^y$, —P(O)$_2$R$^x$, —P(O)(OR$^x$)$_2$, —P(O)(OR$^x$)O$^-$, and —P(O)(O$^-$)$_2$;

wherein the index n is an integer from 0 to 4; and wherein R$^x$, R$^y$ and R$^z$ are independently selected from the group consisting of hydrogen, alkyl, substituted alkyl, alkenyl, substituted alkenyl, aryl, substituted aryl, alkynyl, substituted alkynyl, and R$^u$; R$^u$ is an organic group composed of one or more organic monomers with said monomer molecular weights ranging from 28 to 500; and (b) at least one oxidative hair cream ingredient.

2. The oxidative hair cream composition of claim 1, wherein the composition is a liquid.

3. The oxidative hair cream composition of claim 1, wherein the composition comprises at least one bleaching agent.

4. The oxidative hair cream composition of claim 3, wherein the at least one bleaching agent is a Category 1 bleach.

5. The oxidative hair cream composition of claim 3, wherein the at least one bleaching agent is a Category 2 bleach.

6. The oxidative hair cream composition of claim 1, wherein the at least one oxidative hair cream ingredient is hydrogen peroxide.

7. The oxidative hair cream composition of claim 6, wherein the composition contains from 0.01% to 33% hydrogen peroxide.

8. The oxidative hair cream composition of claim 6, wherein the composition contains from 0.1% to 15% hydrogen peroxide.

9. The oxidative hair cream composition of claim 1, wherein the at least one thiophene azo colorant has a maximum absorbance in the range from 540 nm to 700 nm.

10. The oxidative hair cream composition of claim 1, wherein the ring structure fused with the benzene ring in Formula I is one of naphthalene, tetrahydroquinoline, tetrahydroisoquinoline, indoline, and isoindoline.

11. The oxidative hair cream composition of claim 10, wherein the ring structure is substituted by one or more $R_{16}$ groups.

12. The oxidative hair cream composition of claim 1, wherein two of R$^x$, R$^y$, or R$^z$ are attached to the same carbon or nitrogen group and form the ring structure.

13. The oxidative hair cream composition of claim 12, wherein the ring structure is one of piperazine, piperidine, and pyrrolidine.

14. The oxidative hair cream composition of claim 13, wherein the ring structure is further substituted by one or more $R_{16}$ groups.

15. A method for treating hair comprising the steps of:
(a) providing an oxidative hair cream composition according claim 1, and (b) contacting said oxidative hair cream composition with human hair.

* * * * *